United States Patent
Dave et al.

(10) Patent No.: US 10,736,975 B2
(45) Date of Patent: Aug. 11, 2020

(54) INFUSION ADMINISTRATION OF CONJUGATED MONOCLONAL ANTIBODIES

(71) Applicants: Kaushik J. Dave, Edison, NJ (US); Yulian Zhang, Acton, MA (US)

(72) Inventors: Kaushik J. Dave, Edison, NJ (US); Yulian Zhang, Acton, MA (US)

(73) Assignee: Actinium Pharmaceuticals, Inc., New York, NY (US)

( * ) Notice: Subject to any disclaimer, the term of this patent is extended or adjusted under 35 U.S.C. 154(b) by 18 days.

(21) Appl. No.: 15/575,056

(22) PCT Filed: May 20, 2016

(86) PCT No.: PCT/US2016/033479
§ 371 (c)(1),
(2) Date: Nov. 17, 2017

(87) PCT Pub. No.: WO2016/187514
PCT Pub. Date: Nov. 24, 2016

(65) Prior Publication Data
US 2018/0296708 A1 Oct. 18, 2018

Related U.S. Application Data

(60) Provisional application No. 62/164,601, filed on May 21, 2015.

(51) Int. Cl.
| | | |
|---|---|---|
| *A61K 51/10* | (2006.01) | |
| *C07K 16/28* | (2006.01) | |
| *A61K 47/68* | (2017.01) | |
| *A61P 35/02* | (2006.01) | |
| *A61K 31/427* | (2006.01) | |
| *A61K 31/7036* | (2006.01) | |
| *A61M 5/14* | (2006.01) | |
| *A61M 5/142* | (2006.01) | |
| *A61B 6/00* | (2006.01) | |
| *A61K 9/00* | (2006.01) | |
| *A61K 39/00* | (2006.01) | |

(52) U.S. Cl.
CPC ........ *A61K 51/1027* (2013.01); *A61K 31/427* (2013.01); *A61K 31/7036* (2013.01); *A61K 47/6803* (2017.08); *A61K 47/6809* (2017.08); *A61K 47/6849* (2017.08); *A61K 47/6867* (2017.08); *A61K 51/1069* (2013.01); *A61M 5/14* (2013.01); *A61P 35/02* (2018.01); *C07K 16/2803* (2013.01); *C07K 16/289* (2013.01); *C07K 16/2887* (2013.01); *A61B 6/4057* (2013.01); *A61K 9/0019* (2013.01); *A61K 2039/505* (2013.01); *A61K 2039/54* (2013.01); *A61K 2039/545* (2013.01); *A61M 5/142* (2013.01); *A61M 2005/1403* (2013.01)

(58) Field of Classification Search
None
See application file for complete search history.

(56) References Cited

U.S. PATENT DOCUMENTS

| | | |
|---|---|---|
| 5,762,907 A | 6/1998 | Simon et al. |
| 2003/0229208 A1 | 12/2003 | Queen et al. |
| 2004/0219156 A1 | 11/2004 | Goldenberg et al. |
| 2006/0263357 A1 | 11/2006 | Tedder et al. |
| 2011/0178359 A1 | 7/2011 | Hirschman et al. |
| 2012/0207672 A1* | 8/2012 | Bartz ..................... A61B 6/037 424/1.49 |

OTHER PUBLICATIONS

Morris et al. Pilot trial of unlabeled and indium-111-labeled anti-prostate-specific membrane antigen antibody J591 for castrate metastatic prostate cancer. 2005 Clin. Cancer Res. 11: 7454-7461. (Year: 2005).*
Goldenberg et al. Antibody pretargeting advances cancer radioimmunodetection and radioimmunotherapy. 2006 J. Clin. Oncol. 24: 823-834. (Year: 2006).*
Eary et al. Imaging and treatment of B-cell lymphoma. 1990 J. Nucl. Med. 31: 1257-1268. (Year: 1990).*
Kossman et al. A phase I trial of humanized monoclonal antibody HuM195 (anti-CD33) with low-dose interleukin 2 in acute myelogenous leukemia. 1999 Clin. Cancer Res. 5: 2748-2755. (Year: 1999).*
Dias et al. Tc-99m direct radiolabeling of monoclonal antibody ior egf/r3: quality control and image studies in mice. 2005 Braz. Arch. Biol. Technol. 48: 29-35. (Year: 2005).*
Burke et al., "Cytoreduction with iodine-131-and-CD33 antibodies before bone marrow transplantation for advanced myeloid leukemias", Sep. 30, 2003, vol. 32, Issue 6, pp. 549-556.
Matthews, Dana C. et al., Phase I Study of I-Anti-CD45 Antibody Plus Cyclophosphamide and Total Body Irradiation for Advanced Acute Leukemia and Myelodysplastic Syndrome, Blood, vol. 94, No. 4, p. 1237-1247, 1999.
Buchsbaum, Donald J. et al., Therapy with Unlabeled and I-Labeled Pan-B-Cell Monoclonal Antibodies in Nude Mice Bearing Raji Burkitt's Lymphoma Xenografts, Cancer Research, vol. 52, p. 6476-6481, 1992.

* cited by examiner

*Primary Examiner* — Jennifer Lamberski
(74) *Attorney, Agent, or Firm* — Dentons Cohen & Grigsby P.C.

(57) ABSTRACT

A patient specific therapeutic composition provided in a single dose container, the total volume of which may be administered to a patient in a single treatment session. The composition includes a monoclonal antibody having a labeled fraction and an unlabeled fraction, and a pharmaceutically acceptable carrier. The label may be any of a radioisotope or a drug such as a chemotherapeutic or cytotoxic agent. The amount of the monoclonal antibody and any conjugated label molecule may depend on at least one patient specific parameter selected from a patient weight, a patient age, a patient height, a patient gender, a patient medical condition, and a patient medical history. Methods of administration, production, and articles of manufacture comprising the patient specific therapeutic composition are also disclosed.

19 Claims, 1 Drawing Sheet

INFUSION ADMINISTRATION OF CONJUGATED MONOCLONAL ANTIBODIES

CROSS-REFERENCE TO RELATED APPLICATIONS

The present application is a 35 U.S.C. § 371 national phase application of PCT/US2016/33479 filed on Jul. 7, 2016, titled "Infusion Administration of Conjugated Monoclonal Antibodies" which claims the benefit under 35 U.S.C. § 119(e) of prior U.S. Provisional Application Ser. No. 62/164,601, titled "Infusion administration of Iomab-B" filed on May 21, 2015, and, the content of which is incorporated by reference here into this application.

FIELD OF THE INVENTION

The present invention relates to patient specific doses and administration methods for conjugated monoclonal antibody compositions, and more particularly, to a composition comprising a monoclonal antibody conjugated to an effector molecule which is formulated for single use based on one or more specific patient characteristics, and methods which provide administration and, if needed, in-line dilution of the composition thus reducing exposure of medical personnel to the composition.

BACKGROUND OF THE INVENTION

Although differences in the dosing requirements and procedures for radiotherapeutic, chemotherapeutic, cytotoxic, or drug agents have been recognized, conventional procedures continue to use these agents provided as pre-set doses and volumes. While production of these fixed dose vials is simpler, differences in the actual total dose required for different patients (e.g., based on weight, age, gender, etc.) leads to waste and increases the risks of administration errors. For example, according to best practices, once a bottle of a radiotherapeutic agent is opened for use on a first patient, it may not be used on another patient due to contamination considerations; any unused amount of the radiotherapeutic agent remaining in the vial must be discarded. Such waste is not only expensive, but also poses exposure problems. The unused radiation dose continues to present exposure risks to the medical personnel and patient, and must be properly disposed of or stored within the medical facility.

In certain situations, the radiotherapeutic, chemotherapeutic, cytotoxic, or drug agents are provided as stock formulations having larger volumes, higher concentrations, and/or high specific activities so that they may be used to treat several patients. These stock formulations must be diluted by medical personnel at the hospital or at a compounding pharmacy before administration to individual patients. This step exposes the medical personnel to high radiation doses and/or high concentrations of the chemotherapeutic, cytotoxic or drug agent during the compounding step, and leads to additional contaminated waste. Further, this step increases the risk that the radiotherapeutic, chemotherapeutic, cytotoxic, or drug agent may itself become contaminated or may be improperly formulated, leading to increased risks for the patient.

SUMMARY OF THE INVENTION

The present invention may overcome many of the shortcomings of the prior art by providing a patient specific dose of a monoclonal antibody conjugated to an effector molecule such as, for example, a radiotherapeutic or drug agent (chemotherapeutic, cytotoxic, or other drug agent), that is delivered to a treatment center and may be entirely administered to a single patient in one treatment session. As such, there may be no radiotherapeutic or drug agent remaining as waste, no need for additional dilution or compounding steps to prepare the agent, and/or reduced exposure of medical personnel to the agent. Furthermore, the patient specific dose of the radiotherapeutic or drug agent may be administered using systems and protocols which promote reduced waste and risks compared to the conventional methods and systems.

The present invention provides a patient specific therapeutic composition which may be included in a single dose container, the total volume of which may be administered to a patient in a single treatment session. The composition includes a monoclonal antibody having a labeled fraction and an unlabeled fraction, and a pharmaceutically acceptable carrier. The labeled fraction may include an effector molecule conjugated to the monoclonal antibody, wherein the effector molecule may comprise a radiotherapeutic agent or a drug agent such as, for example, a chemotherapeutic, cytotoxin, drug, or a combination thereof.

A dose of the effector molecule of the labeled fraction of the monoclonal antibody and a total protein amount of the monoclonal antibody may depend on at least one patient specific parameter. Patient specific parameters include, but are not limited to, a patient weight, a patient age, a patient height, a patient gender, a patient medical condition, and a patient medical history.

Exemplary radiotherapeutic effector molecules include beta emitters such as, for example, $^{131}$I, $^{90}$Y, $^{177}$Lu, $^{186}$Re, or $^{188}$Re, and gamma emitters such as, for example, $^{125}$I or $^{123}$I. Exemplary drug agents include chemotherapeutic effector molecules such as, for example, microtubule stabilizing agents such as taxans (docetaxel, paclitaxel) or epothilones (epothilone A, B, C, D, E, or F), microtubule destabilizing agents such as *vinca* alkaloids (vinblastine, vincristine, vindesine, vinflunine, vinorelbine, etoposide), methotrexate, antibiotics (adriamicin, doxorubicin, mitomycin C), alkylating agents (melphalan, chlorambucil), antineoplastics agents (daunorubicin), or other intercalating agents (calicheamicin). Exemplary drug agents further include cytotoxic effector molecules such as, for example, abrin, ricin, *Pseudomonas* exotoxin (PE), diphtheria toxin (DT), botulinum toxin, or modified toxins thereof. Exemplary drug agent effector molecules may further include mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

According to certain aspects of the invention, the monoclonal antibody may be an antibody useful for the treatment of a lymphoma or leukemia. For example, the monoclonal antibody may be useful as a medicament for the ablation of bone marrow cells in cancer patients to prepare them for donor bone marrow transplant, or in the treatment of a leukemia such as, for example, Acute Myeloid Leukemia (AML). For example, the monoclonal antibody may be an antibody against CD45, such as BC8, an antibody against CD33, such as HuM195, or an antibody against CD20.

When the amount of the monoclonal antibody included in the composition depends on a patient specific characteristic, such as patient weight, an exemplary protein content for a composition comprising the monoclonal antibody includes a dosimetry dose comprising a total protein amount of between 1 mg and 60 mg, such as between 10 mg and 50 mg, or between 25 mg and 45 mg, or a therapeutic dose comprising a total protein amount of between 0.2 mg/kg patient weight to 10.0 mg/kg patient weight, such as 0.2 mg/kg to 2.0 mg/kg, or 0.4 mg/kg to 0.6 mg/kg, or 0.5 mg/kg.

When the effector molecule is a radioisotope, the dosimetry dose may comprise radiation dose between 0.1 milliCuries to 30 milliCuries of a beta emitter, and the therapeutic dose may comprise a radiation dose of between 30 milliCuries and 2000 milliCuries, such as between 50 milliCuries and 1500 milliCuries, or even between 100 milliCuries and 1200 milliCuries of a beta emitter.

When the effector molecule is a drug agent, such as a chemotherapeutic agent, cytotoxic agent, or other drug agent, the dose administration to the patient in a single infusion session may be in the range of 1 to 500 mg/m$^2$, the amounts being calculated as a function of patient surface area (m$^2$). For example, exemplary doses of paclitaxel may include 15 mg/m$^2$ to 275 mg/m$^2$, exemplary doses of docetaxel may include 60 mg/m$^2$ to 100 mg/m$^2$, exemplary doses of epithilone may include 10 mg/m$^2$ to 20 mg/m$^2$, and an exemplary dose of calicheamicin may include 1 mg/m$^2$ to 10 mg/m$^2$. While exemplary doses are listed herein, such are only provided for reference and are not intended to limit the dose ranges of the drug agents of the presently disclosed invention. These doses may be generally formulated in volumes of between 5 mL and 100 mL.

The present invention also provides a method of administration of the patient specific therapeutic compositions described above which may include administering the total volume of the patient specific therapeutic composition to a patient through a fluid path, and flushing the fluid path with normal saline after administration of the therapeutic composition. The compositions may be administered intravenously, intramuscularly, or subcutaneously to the patient at a rate of between 0.01 mg to 10 mg monoclonal antibody per hour, such as a rate of between 1 mg to 8.5 mg monoclonal antibody per hour, such as at a rate of about 7.5 mg monoclonal antibody per hour. Further, the presently disclosed system and methods provide means for in-line dilution of the composition with a pharmaceutically acceptable carrier, such as saline. After administration, no measurable volume of the patient specific therapeutic composition may remain in the fluid path. Further, all components used for administration of the therapeutic composition may be safely discarded.

The patient specific therapeutic composition of the present invention allows for automation of the administration software used by a pump system. Since the dose is tailored to each patient, and the volume of the composition may be constant, the medical personnel may need only attach a container comprising the composition to a fluid delivery system, such as disclosed herein, and start the infusion. This may reduce the risks mentioned above related to incorrectly diluted or contaminated of the composition during dilution, and may reduce the exposure that medical personnel experience in executing an infusion procedure for a patient.

The present invention also provides a method for production of the patient specific therapeutic compositions described above which may include formulating the patient specific therapeutic composition as a patient specific dose in a total volume of between 5 mL and 100 mL, and providing the patient specific dose in a container having a sterile access port. When the effector molecule is a radiotherapeutic agent, the container may be radiation shielded or stored within a radiation shielded outer vessel. The patient specific therapeutic composition may be frozen to a temperature ≤−20° C.

The present invention also provides an article of manufacture which may include a container having a sterile access port and comprising a patient specific therapeutic composition as described above provided as a patient specific dose. The patient specific therapeutic composition comprises a monoclonal antibody comprising a labeled fraction and an unlabeled fraction, and a pharmaceutically acceptable carrier. The labeled fraction may include the monoclonal antibody conjugated to an effector molecule such as a radiotherapeutic or drug agents (chemotherapeutic, cytotoxic, or drug agent). The article of manufacture may also include a label or package insert on or associated with the container. When the effector molecule is a radiotherapeutic agent, the container may be radiation shielded or stored within a radiation shielded outer vessel.

BRIEF DESCRIPTION OF THE DRAWINGS

Aspects, features, benefits and advantages of the embodiments herein will be apparent with regard to the following description, appended claims, and accompanying drawing. It is to be noted that features and components in this drawing, illustrating a view of an embodiment of the present invention, unless stated to be otherwise, are not necessarily drawn to scale.

DEFINITIONS AND ABBREVIATIONS

Throughout this description and in the appended claims, use of the singular includes the plural and plural encompasses singular, unless specifically stated otherwise. For example, although reference is made herein to "an" antibody, "an" effector molecule, "a" pharmaceutical carrier, and "a" composition, one or more of any of these components and/or any other components described herein may be used.

The word "comprising" and forms of the word "comprising", as used in this description and in the claims, does not limit the present invention to exclude any variants or additions. Additionally, although the present invention has been described in terms of "comprising", the processes, materials, and compositions detailed herein may also be described as consisting essentially of or consisting of. For example, while certain aspects of the invention have been described in terms of a composition comprising a monoclonal antibody and a pharmaceutically acceptable carrier, a composition "consisting essentially of" or "consisting of" a monoclonal antibody and a pharmaceutically acceptable carrier is also within the present scope. In this context, "consisting essentially of" means that any additional components will not materially affect the immunological reactivity of the monoclonal antibody or the efficacy of the effector molecule.

Moreover, other than in the examples, or where otherwise indicated, all numbers expressing, for example, quantities of ingredients used in the specification are to be understood as being modified in all instances by the term "about". Accordingly, unless indicated to the contrary, the numerical parameters set forth in the following specification are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements. When ranges are given, any endpoints of those ranges and/or numbers within those ranges can be combined within the scope of the present invention.

An "effector molecule" may be any of a radiotherapeutic or drug agent which may be conjugated to a monoclonal antibody so that it may be targeted to a specific tissue or population of cells and may produce an effect on that tissue or cell population. For example, a radiotherapeutic agent includes a radiolabel such as a beta emitter ($^{131}$I, $^{90}$Y, $^{177}$Lu, $^{186}$Re, $^{188}$Re) or gamma emitter ($^{125}$I, $^{123}$I). The terms effector molecule and label are used interchangeably within the following description. Furthermore, the term "radiotherapeutic" may be taken to more broadly encompass any radioactively-labeled moiety, and may include any pharmaceutical associated with or comprising a radionuclide. The pharmaceutical may be associated with a radionuclide through a chelator, direct chemical bonding, or some other means such as a linker protein, scaffold or molecule.

The monoclonal antibody may be conjugated to an effector molecule such as a drug agent, thus forming an antibody drug conjugate (ADC). The drug agent may be any chemotherapeutic agent, cytotoxin, or other drug, and may be associated with or be attached to the monoclonal antibody through a chelator, via direct chemical bonding, or some other means such as a linker protein, scaffold or other molecule. Furthermore, certain drug agents may be conjugated with the monoclonal antibody using intracellularly cleavable linkages, such as linkages that are cleavable by specific intracellular enzymes or under the acidic pH of certain intracellular compartments.

"Cytotoxins" may generally include small molecule toxins or enzymatically active toxins of bacterial, fungal, plant or animal origin, including fragments and/or variants thereof. Examples of cytotoxic agents include, but are not limited to, abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin and replacing it with a different targeting moiety, such as a monoclonal antibody of the present invention.

"Chemotherapeutic", in the context of this invention, shall mean a chemical compound which inhibits or kills growing cells and which can be used or is approved for use in the treatment of cancer. Exemplary chemotherapeutic agents include cytostatic agents which prevent, disturb, disrupt or delay cell division at the level of nuclear division or cell plasma division. Such agents may stabilize microtubules, such as taxanes, in particular docetaxel or paclitaxel, and epothilones, in particular epothilone A, B, C, D, E, and F, or may destabilize microtubules such as *vinca* alcaloids, in particular vinblastine, vincristine, vindesine, vinflunine, and vinorelbine.

As used herein, the terms "antibody," "antibodies," and "immunoglobulins" refer to antibodies, including full-length monoclonal antibodies and polyclonal antibodies. These could be murine antibodies, human antibodies, humanized antibodies, chimeric antibodies, Fab fragments, F(ab')$_2$ fragments, antibody fragments with the desired biological activity, and epitope-binding fragments of any of the above. Immunoglobulin molecules may be of any type such as, IgA, IgD, IgE, IgG, and IgM.

An "epitope" refers to the target molecule site that is capable of being recognized by, and bound by, an antibody. For a protein epitope, this may refer to the amino acids (particularly amino acid side chains) that are bound by the antibody. Overlapping epitopes include at least 1 to 5 common amino acid residues. Methods of identifying epitopes of antibodies are known to those skilled in the art.

The term "isolated antibody" refers to a protein or peptide produced from cDNA-, recombinant RNA-, cell fusion product, any other synthetic origin, or some combination thereof.

The term "monoclonal antibody" as used herein refers to an antibody composition of substantially identical molecules except for allowing for minor amounts of possible naturally occurring mutations as well as post translational modification such as deaminations of Asn and Gln, methionine oxidation, pyroglutamic acid formation and loss of C-terminal Lys from the heavy chains. Furthermore, a monoclonal antibody is directed towards a single determinant (epitope) on the antigen which is in contrast to a polyclonal antibody preparation consisting of a pool of antibodies directed against different epitopes of an antigen. The monoclonal antibodies are synthesized by hybridoma cells that are uncontaminated by other immunoglobulin producing cells, or by stably or transiently transfecting host cells with the heavy and light chain genes encoding the monoclonal antibody.

An "antigen" refers to one or more molecules of one or more portions of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens. The binding of the antigen to antibody must be above background levels.

"Immunoreactivity" refers to a measure of the ability of an immunoglobulin to recognize and bind to a specific antigen.

As used herein, the term "Therapeutic Dose" refers to an immunoglobulin conjugated with an effector molecule in a dose sufficient to provide a desired therapeutic dose to the target tissue or organ upon administration to a subject or patient. As used herein, the term "Dosimetry Dose" refers to an immunoglobulin radiolabeled with sufficient radioactivity that may be capable of providing an in vivo biodistribution to various organs as well as the pharmacokinetic profile to help ascertain a subsequent therapeutic dose of the radiolabeled immunoglobulin for the subject or patient in need thereof. In the present invention, a dosimetry dose is administered to a subject to estimate distribution in the body so that a radiotherapy dose (Therapeutic Dose) may be estimated.

Unless otherwise defined, all technical and scientific terms used herein have the same meaning as commonly understood by one of ordinary skill in the art to which this present invention belongs. Although methods and materials similar or equivalent to those described herein can be used in the practice or testing described herein, suitable methods and materials are described below.

DETAILED DESCRIPTION

The present invention provides patient specific therapeutic compositions, methods of their use and production, and articles of manufacture comprising the patient specific therapeutic compositions. As indicated above, standard therapeutic agents are supplied in pre-set dose formulations. In general, a portion of such a formulation is removed and administered directly to a patient, or is diluted or compounded with other agents prior to administration. In both scenarios, the medical personnel experiences increased exposure to the radioactive or toxic compounds therein, and the composition to be administered to the patient experience increased risks of contamination from the local environment (e.g., biologic). Further, each additional step in preparing the therapeutic agent produces additional contaminated waste (e.g., radioactive or toxic), and increases the potential that the dose may be incorrectly formulated.

A patient specific therapeutic composition provided in a single dose container may solve the aforementioned problems. Each dose is formulated and provided in a single use container that may be delivered directly to the treatment center prior to use. A dose of an effector molecule and the total protein content for each dose may be tailored to at least one patient specific parameter, such as a patient weight, a patient age, a patient height, a patient gender, a patient medical condition, or a patient medical history. As such, administration of the patient specific therapeutic composition may be as simple as placing the container comprising the composition in-line on a fluid delivery path, such as the fluid delivery path and system shown in FIG. 1. Additional sources of pharmaceutically suitable carriers such as, for example, saline, may also be placed in-line on the fluid delivery path, and may be used to: (a) ensure full delivery of the composition from the container and/or the fluid lines of the fluid delivery path; (b) control the rate of delivery of the composition; (c) provide dilution of the monoclonal antibody in the patient specific therapeutic composition; and/or (d) flush the fluid lines of the fluid delivery path after administration of the composition is successfully completed.

All components used for administration of the therapeutic composition are in one location and are minimally contaminated as the full dose, or nearly the full dose, of the composition may have been delivered to the patient. Thus, clean up following an administration procedure is minimized and presents fewer overall risks to the medical personnel.

Further, compositions comprising very high doses of the effector molecule, such as high specific activity radiolabeled monoclonal antibody, and/or very high concentrations of the monoclonal antibody, may be diluted in-line using the methods and infusion system of the present invention. Such in-line dilution may provide a means to at least: (a) stabilize the patient specific therapeutic composition, as compositions comprising higher protein concentrations (0.02 mg/ml to 100 mg/ml) tend to be more stable that those that are very dilute (<0.02 mg/ml), (b) minimize a patient's adverse reaction to the high concentration of the monoclonal antibody and/or effector molecule, and/or (c) reduce exposure and risks associated with dose preparation at the treatment center (as discussed above).

Figure 1:
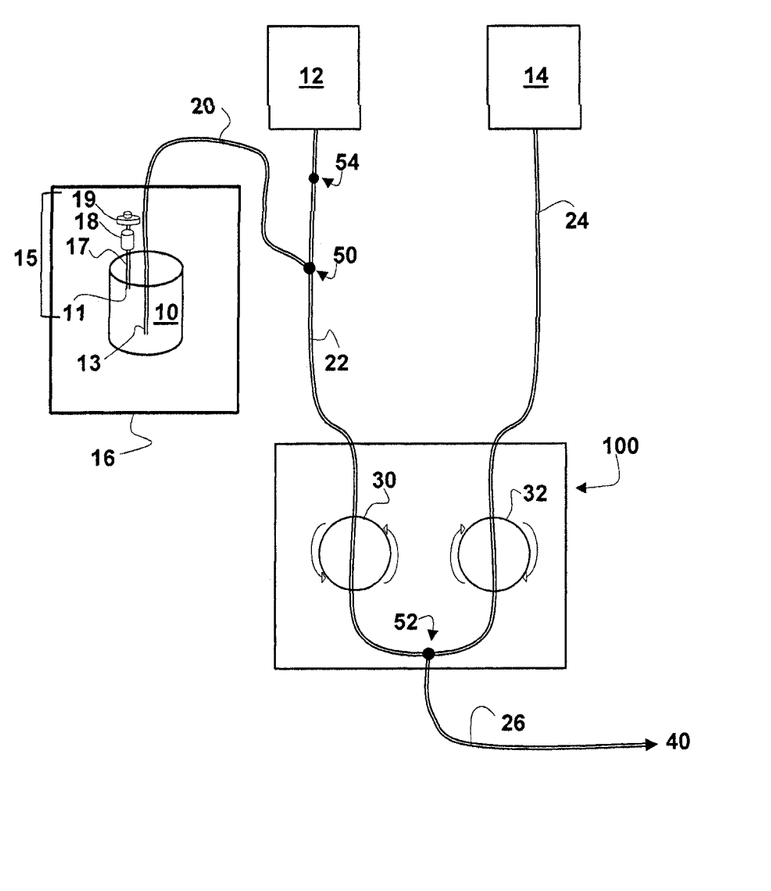
FIG. 1 illustrates a fluid path for administration of a patient specific therapeutic composition according to certain aspects of the present invention.

With reference to FIG. 1, the patient specific therapeutic composition of the present invention may be provided in a container 10 comprising a sterile port or septum that may be pierced by a cannula. The cannula may include a portion of tubing (first fluid path element 20) which may connect to a fluid delivery path at a junction 50. In general, the length of the first fluid path element 20 that connects the container 10 to the fluid delivery path should be minimized to reduce waste. A first liquid carrier source 12, which may generally contain a pharmaceutically acceptable fluid such as saline, may be connected to the fluid delivery path via tubing (second fluid path element 22) which connects to a patient delivery line (third fluid path element 26) via another junction 52 for delivery to the patient 40. The second fluid path element 22 may be attached to an infusion system 100 which may use a pump 30 to initiate and regulate flow of the first liquid carrier 12 through the second fluid path element 22 and downstream portions of the fluid delivery path.

Further, a second liquid carrier source 14, which may be a pharmaceutically acceptable liquid such as saline, may be connected to the fluid delivery path via tubing (forth fluid path element 24) which connects to the third fluid path element 26 via another junction 52. The forth fluid path element 24 may be attached to an infusion system 100 which may use a pump 32 to initiate and regulate flow of the second liquid carrier 14 through the forth fluid path element 24 and downstream portions of the fluid delivery path.

The first and second liquid carrier sources (12, 14) may include saline, as mentioned, or any other pharmaceutically acceptable liquid such as, for example, glucose. Additionally, the liquid carrier sources may be used to provide additional therapeutic agents which may be delivered before, after, or at the same time as the patient specific therapeutic compositions of the present invention.

The junctions (50, 52) provide connection of the first and third fluid delivery path elements (20, 26) to upstream fluid sources such as the first and second liquid carriers (12, 14) via the second and forth fluid path elements (22, 24). Optional valve elements may be included at the junctions (50, 52) to provide fluid flow control and may be, for example, one way check valves or slit silicone diaphragm valves which prevent diffusion and/or gravity driven movement of liquid in the fluid path elements (20, 22, 24, 26). Additionally, these valve elements may be manual or electronic, such as pinch valves or rotary valves. An additional junction 54 may be placed on the second fluid path element 22 that leads from the first carrier liquid source 12, such as above the junction 50 with the first fluid path element 20. This additional junction 54 may be used to regulate or stop the flow of fluid from the first carrier liquid source 12, and may be a manual or electronic valve, or may be a simple as a roller clamp or A-clamp.

In instances when the patient specific therapeutic composition comprises an effector molecule which is a therapeutic, the container 10 comprising the patient specific therapeutic composition may comprise a radiation shielded container, or may be placed inside of a radiation shielded outer container 16. Alternatively, the container 10 may be placed behind radiation shielding configured as a barrier (e.g., wall) or other compartment.

The container 10 may comprise a septum which may be sterile and may be pierced by a cannula 13 attached to an end of the first fluid path element 20 to gain access to the composition therein. In general, the cannula 13 may be extended within the container 10 to a bottom thereof. Due to variations in the temperature during delivery and storage of the patient specific therapeutic composition, the container 10 may develop an internal pressure that may need to be vented. As such, the container 10 may be initially pierced by a cannula 11 attached to an end of a vent unit 15 which may include a fluid line 17, an absorbent cartridge 18, and a filter cartridge 19. The cannula 11 may be placed at a position above the fluid level within the container 10. The vent unit 15, and in particular the absorbent cartridge 18, may be included to capture any volatilized radioactivity or toxic agent.

Further, during administration of the patient specific therapeutic composition, the container 10 may experience a negative internal pressure. The vent unit 15, and in particular the filter cartridge 19, may allow the pressure to equalize while maintaining the sterility of the composition in the container 10. While portions of the vent unit 15 are shown in a specific configuration, other configurations and components that achieve the same result are within the scope of the present invention.

Thus, the present invention provides a system for administration of a patient specific therapeutic composition. The system may comprise a first fluid path element 20 which may connect a container 10 including the patient specific therapeutic composition with a second fluid path element 22. The second fluid path element 22 may provide connection between a first liquid carrier source 12, an infusion system 100, and a third fluid delivery path element 26, and may allow flow of fluids from the first liquid carrier source 12 and the container 10 to be directed for delivery to a patient. The system may further comprise a forth fluid path element 24 that may provide connection between a second liquid carrier source 14, the infusion system 100, and the third fluid delivery path element 26, and may allow flow of fluids from the second liquid carrier source 14 to be directed for delivery to a patient. The infusion system 100 may be used control delivery of fluids from the container 10, and first and second liquid carrier sources (12, 14) individually or in combination. As such, the patient specific therapeutic composition may be administered to the patient diluted or undiluted.

A method of administration of the patient specific therapeutic composition of the present invention thus includes administering the total volume of the patient specific therapeutic composition to a patient through a fluid delivery path, wherein the fluid path includes a therapeutic agent specific portion, such as the first fluid delivery path element 20. After administration of the composition, a second fluid delivery path element 22 may be flushed with fluid from the first carrier liquid source 12 to ensure delivery of any residual amount of the composition that may remain in the fluid delivery path (fluid path elements 22 and 26). In this way, all or almost all of the composition may be deliverable to the patient such that no measurable volume of the patient specific therapeutic composition may remain in the fluid path.

The patient specific therapeutic composition may be formulated and frozen for storage prior to delivery and/or use at a medical or treatment center. Storage may be at a temperature below freezing such as, for example, −20° C., −40° C., −70° C., or even −80° C. Prior to use, the composition may be thawed to ambient conditions. "Ambient conditions" may be taken to mean the condition of surroundings without adjustment of the temperature, humidity or pressure. Usually ambient temperature ranges from 60° F. to 90° F. (15.6° C. to 32.2° C.), such as a typical room temperature, 72° F. (22.2° C.). The composition may be thawed to ambient conditions for at least an hour, such as at least two hours, 1 to 5 hours, or 2.5 hours.

The patient specific therapeutic composition may be administered intravenously, intramuscularly, or subcutaneously to the patient. Typical administration rates for the compositions may be between 0.1 mg and 10 mg of protein (e.g., monoclonal antibody) per hour, such as between 1 mg and 8.5 mg of protein per hour, or even about 7.5 mg of protein per hour.

According to certain aspects of the present invention, the effector molecule may include a radiotherapeutic agent. Thus, in the practice of the methods of the invention, the patient specific therapeutic composition may be administered to the patient at a dosimetric evaluation stage and a therapeutic treatment stage. Generally, a single radiotherapeutic, usually radiolabeled in differing amounts (typically a high milliCurie amount for delivery of a therapeutically effective amount of radioactivity and a relatively small milliCurie amount for an earlier dosimetric evaluation) is used for patient specific dosimetry and for treatment.

As such, the patient specific therapeutic compositions of the present invention may comprise a monoclonal antibody comprising a radiolabeled fraction and an unlabeled fraction, and a pharmaceutically acceptable carrier. A radiation dose of the labeled fraction of the monoclonal antibody and a total protein amount of the monoclonal antibody may depend on at least one patient specific parameter, wherein the at least one patient specific parameter includes a patient weight, a patient age, a patient height, a patient gender, a patient medical condition, and a patient medical history. Further, a total volume of the patient specific radiotherapeutic agent may be wholly deliverable to a patient in one treatment session. The radiolabel may be a beta emitter such as, for example, any one or combination of $^{131}$I, $^{125}$I, $^{90}$Y, $^{177}$Lu, $^{186}$Re, and $^{188}$Re, or a gamma emitter such as, for example, $^{125}$I or $^{123}$I.

According to certain aspects of the present invention, the effector molecule may include a drug, thus providing an antibody drug conjugate (ADC). Exemplary drug effector molecules include chemotherapeutic agent such as a taxan (docetaxel, paclitaxel), epothilone (epothilone A, B, C, D, E, or F), vinca alkaloid (vinblastine, vincristine, vindesine, vinflunine, vinorelbine, etoposide), methotrexate, antibiotic (adriamicin, doxorubicin, mitomycin C), alkylating agent (melphalan, chlorambucil), antineoplastic agent (daunorubicin), or other intercalating agent.

Exemplary drug effector molecules further include cytotoxic molecules such as abrin, ricin, Pseudomonas exotoxin (PE), diphtheria toxin (DT), botulinum toxin, or modified toxins thereof.

Furthermore, the effector molecule may include a drug agent such as mitotic inhibitors, antitumor antibiotics, immunomodulating agents, vectors for gene therapy, alkylating agents, antiangiogenic agents, antimetabolites, boron-containing agents, chemoprotective agents, hormones, anti-hormone agents, corticosteroids, photoactive therapeutic agents, oligonucleotides, radionuclide agents, topoisomerase inhibitors, tyrosine kinase inhibitors, and radio-sensitizers.

According to certain aspects of the invention, the monoclonal antibody may be an antibody useful for the treatment of a lymphoma or leukemia. For example, the monoclonal antibody may be useful as a medicament for the ablation of bone marrow cells in cancer patients to prepare them for donor bone marrow transplant, or in the treatment of leukemia such as, for example, Acute Myeloid Leukemia (AML). For example, the monoclonal antibody may be an antibody against CD45, such as BC8, an antibody against CD33, such as HuM195, or an antibody against CD20.

When the amount of the monoclonal antibody included in the composition depends on a patient specific characteristic such as patient weight, an exemplary protein content for a composition comprising the monoclonal antibody include a dosimetry dose comprising a total protein amount of between 5 mg and 50 mg, such as between 25 mg and 45 mg, or a therapeutic dose comprising a total protein amount of between 0.2 mg/kg patient weight to 10.0 mg/kg patient weight, such as 0.2 mg/kg to 2.0 mg/kg, or even 0.4 mg/kg to 0.6 mg/kg, or 0.5 mg/kg.

When the effector molecule is a radioisotope, the dosimetry dose may comprise a radiation dose of between 0.1 milliCuries and 30 milliCuries of a beta emitter (such as $^{131}$I), and the therapeutic dose may comprise a radiation dose of between 30 milliCuries and 2000 milliCuries, such as between 50 milliCuries and 1500 milliCuries, or even between 100 milliCuries and 1200 milliCuries of a beta emitter.

When the effector molecule is a chemotherapeutic agent, cytotoxic agent, or drug agent, the dose administered to the patient per administration session may be high enough to be effective, but must be below the dose limiting toxicity (DLT). In general, a sufficiently well tolerated dose below DLT will be considered maximum tolerated dose (MTD). A skilled artisan knows how to determine the MTD for each agent. In general, the MTD may be expected to be in the range of 1 mg/m$^2$ to 500 mg/m$^2$, the amounts being calculated as a function of patient surface area (m$^2$). For example, exemplary doses of paclitaxel may include 15 mg/m$^2$ to 275 mg/m$^2$, exemplary doses of docetaxel may include 60 mg/m$^2$ to 100 mg/m$^2$, exemplary doses of epithilone may include 10 mg/m$^2$ to 20 mg/m$^2$, and exemplary doses of calicheamicin may include 1 mg/m$^2$ to 10 mg/m$^2$.

The total volume of the patient specific therapeutic composition may be any volume between 5 mL to 100 mL, such as 25 mL to 75 mL, 40 mL to 50 mL, or 45 mL. Limitations on the volume may depend on transport considerations, solubility of the various components of the composition, and preparation (thawing) consideration. Volumes which are too small, such as below 5 mL, may be difficult to deliver, and volumes which are too large, such as over 250 mL, may be slow to thaw and/or difficult to safely transport.

According to certain aspects of the present invention, the patient specific therapeutic composition may comprise a monoclonal antibody that binds specifically to a CD45 antigen, such as BC8. The composition may therefore be useful as a medicament for the ablation of bone marrow cells in cancer patients to prepare them for donor bone marrow transplant. An exemplary labeled monoclonal antibody includes $^{131}$I-BC8, wherein the radiation dose may be a dosimetry dose of up to 30 milliCuries, and may include a total protein amount of between 25 mg and 45 mg. Alternatively, the $^{131}$I-BC8 may be provided as a therapeutic dose of between 100 milliCuries and 1500 milliCuries with a total protein amount of between 0.4 mg/kg patient weight to 0.6 mg/kg patient weight, such as 0.5 mg/kg patient weight.

The CD45 antigen is a member of the protein tyrosine phosphatase (PTP) family and is a 180-240 kD transmembrane glycoprotein. It is also known as the leukocyte common antigen (LCA), T200, or Ly-5. CD45 plays a key role in T-cell and B-cells receptor signal transduction. Different isoforms of CD45 exist due to variable splicing of its exons. These isoforms are very specific to the activation and maturation state of the cell as well as cell type. The various isoforms have the same transmembrane and cytoplasmic segments, but different extra-cellular domains and are differentially expressed on subpopulations of B- and T-cell lymphocytes. The primary ligands described for CD45 include galectin-1, CD1, CD2, CD3, CD4, TCR, CD22, and Thy-1.

Depending on which of the alternatively spliced exons (A, B or C) is recognized, antibodies restricted to recognizing one or the other isoform have been identified (termed CD45R). In addition, monoclonal antibodies (mAbs) binding an epitope common to all the different isoforms have also identified. The mAbs designated CD45RA recognize the product of exon-A. The mAbs designated CD45RB recognize the product of exon-B. A third type of mAbs termed CD45RO (as exemplified by UCHL1) selectively bind to the 180 kDa isoform (without any of the variable exons A, B or C) which is restricted to a subset of cortical thymocytes, activated T cells and memory cells, and is absent on B cells.

In general, all cells of hematopoietic origin, with the exception of mature erythrocytes and platelets, express CD45. High expression of CD45 is seen with most acute lymphoid and myeloid leukemias. Since the CD45 is not found on tissues of non-hematopoietic origin, its specific expression in leukemia makes it a good target for developing therapeutics, including radio-immunotherapeutics. For example, CD45 is expressed at a density of approximately 200,000 to 300,000 sites per cell on circulating leukocytes and malignant B cells. $^{131}$I-labeled anti-CD45 antibody (BC8) has been explored as a candidate radio-immunotherapeutic alone and in combination with chemotherapy or total body irradiation. The use of this $^{131}$-anti-CD45 antibody for the treatment of subjects needing bone marrow transplant has also been explored.

Among several clones of the anti-CD45 murine antibody, BC8 recognizes all the human isoforms of the CD45 antigen. The anti-CD45 antibody has been shown to bind to all the isoforms of human CD45 and thus provides an excellent target for the development of therapeutics for certain human malignancies of hematopoietic origin, including lymphomas. Anti-CD45 radiolabeled with $^{131}$I has a short half-life (half-life of $^{131}$I is 8.02 days). Thus, the compositions and methods of the present invention may provide an excellent means to allow high specific activity formulations of $^{131}$I-BC8 to be produced which are specific to a single patient, and which are shipped to a treatment center close to a proposed administration date, such as within 8 days, or 6 days, or even 4 days or less prior to administration.

According to certain aspects of the present invention, the monoclonal antibody may be an antibody that binds specifically to a CD33 antigen, such as HuM195. As such, the composition may be useful as a medicament for the treatment of Acute Myeloid Leukemia. An exemplary composition includes a monoclonal antibody HuM195, a portion of which is labeled with an effector molecule such as the intercalating agent calicheamicin, which may include in a therapeutic dose of between 1 mg/m$^2$ to 10 mg/m$^2$, calculated based on the surface area of a specific patient. Alternatively, the composition may include the monoclonal antibody HuM195, a portion of which is labelled with a beta emitter, wherein the radiation dose may be a dosimetry dose of between 0.1 milliCuries and 30 milliCuries, and may include a total protein amount of between 25 mg and 45 mg, or the radiation dose may be a therapeutic dose of between 30 milliCuries and 2000 milliCuries, such as between 50 milliCuries and 1500 milliCuries, or even between 100 milliCuries and 1200 milliCuries of the beta emitter, and a total protein amount of between 0.4 mg/kg patient weight to 0.6 mg/kg patient weight, such as 0.5 mg/kg patient weight.

The CD33 antigen is a 67 KD transmembrane glycoprotein. The sialic acid-binding extracellular domain of CD33 is involved in cell-cell adhesion. The intracellular immunoreceptor tyrosine-based inhibitory motifs (ITIM) confer inhibitory signals to the cell, affecting proliferation and cell survival. The actual signaling pathways of CD33 are poorly understood but are assumed to involve the ITIM and ITIM-like motifs and the recruitment of tyrosine phosphatases.

CD33 has been described as a stable cell surface marker on primary acute myeloid leukemia and chronic myeloid leukemia cells expressed by 70-100% of tested patients. CD33 is expressed on malignant myeloid blast cells, which represent the majority of malignant cells in peripheral blood and bone marrow of leukemia patients, and on leukemic stem cells, a relatively small number of less differentiated cells in the bone marrow which are characterized by their capacity for self-renewal and the maintenance of the leukemic clonal hierarchy. CD33-positive hematological malignancies include, but are not limited to, acute myeloid leukemia, chronic myeloid leukemia, chronic myelomonocytic leukemia, thrombocyte leukemia, a myelodysplastic syndrome, a myeloproliferative disorder, refractory anemia, a preleukemia syndrome, a lymphoid leukemia, or an undifferentiated leukemia. Thus, monoclonal antibodies directed against CD33 may be used for therapeutic targeting of leukemia, such as in vitro purging of bone marrow for autologous transplantation in acute myeloid leukemia. Depletion of leukemic stem cells is regarded the key mechanism for sustained tumor free survival. Thus, a radiolabeled CD33 may provide a treatment for acute myeloid leukemia patients by specifically delivering radiation to CD33 positive acute myeloid leukemia cells.

According to certain aspects of the present invention, the monoclonal antibody may include an antibody that recognizes the CD20 or CD22 antigens. The CD20 molecule (also called human B-lymphocyte-restricted differentiation antigen or Bp35) is a hydrophobic transmembrane protein located on pre-B and mature B lymphocytes that has been described extensively. CD20 is expressed on greater than 90% of B cell non-Hodgkin's lymphomas (NHL) but is not found on hematopoietic stem cells, pro-B cells, normal plasma cells, or other normal tissues.

There are two different types of antibodies that recognized the CD20 antigen, each differing significantly in the mode of CD20 binding and biological activity. Type I antibodies (e.g., rituximab—a non-afucosylated antibody with an amount of fucose of 85% or higher), are potent in complement mediated cytotoxicity. Type II antibodies (e.g. Tositumomab), effectively initiate target cell death via caspase-independent apoptosis with concomitant phosphatidylserine exposure.

Other B-cell antigens, such as CD19, CD22, and CD52, represent targets of therapeutic potential for treatment of lymphoma. CD22, for example, is a 135-kDa B-cell-restricted sialoglycoprotein expressed on the B-cell surface only at the mature stages of differentiation. In B-cell NHL, CD22 expression ranges from 91% to 99% in the aggressive and indolent populations, respectively. As such, antibodies that bind the CD22 antigen may provide therapies for B cell cancers and other B cell proliferative diseases.

While specific monoclonal antibodies have been listed above and indicated as useful in the present invention, a wide range of monoclonal antibodies may be suitable in the practice of the present invention. As such, the various aspects of the present invention should not be limited to the specific monoclonal antibodies discussed herein, but may include any of a wide range on monoclonal antibodies that may be useful in the treatment of a disease. That is, any monoclonal antibody that may recognize or bind to markers or tumor-associated antigens that are expressed at high levels on target cells and that are expressed predominantly or only on diseased cells versus normal tissues may be useful. Exemplary monoclonal antibodies may include at least the following: LL1 (anti-CD74), LL2 (anti-CD22), RS7 (anti-epithelial glycoprotein-1(EGP-1)), PAM-4 and KC4 (both anti-MUC1), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 (anti-PSMA (prostate-specific membrane antigen)), G250 (an anti-carbonic anhydrase IX mAb) and L243 (anti-HLA-DR). Other useful antigens that may be targeted using these conjugates include HER-2/neu, BrE3, CD19, CD20 (e.g., C2B8, hA20, 1F5 Mabs) CD21, CD23, CD80, alpha-fetoprotein (AFP), VEGF, EGF receptor, P1GF, MUC1, MUC2, MUC3, MUC4, PSMA, gangliosides, HCG, EGP-2 (e.g., 17-1A), CD37, HLA-DR, CD30, Ia, A3, A33, Ep-CAM, KS-1, Le(y), S100, PSA (prostate-specific antigen), tenascin, folate receptor, Thomas-Friedenreich antigens, tumor necrosis antigens, tumor angiogenesis antigens, Ga 733, IL-2, IL-6, T101, MAGE, antigen to which L243 binds, CD66 antigens, i.e. CD66a-d or a combination thereof.

The patient specific therapeutic compositions may be administered by any suitable means, including parenteral, subcutaneous, intraperitoneal, and intrapulmonary, and, if desired for local immunosuppressive treatment, intralesional administration. Parenteral infusions include intramuscular, intravenous, intraarterial, intraperitoneal, or subcutaneous administration. In addition, the antibody composition may suitably be administered by pulse infusion, e.g., with declining doses of the antibody.

Additionally, other compounds may be administered, such as naked (non-immunoconjugated) chemotherapeutic agents, immunosuppressive agents and/or cytokines with the monoclonal antibodies of the patient specific radiotherapeutic compositions disclosed herein. The combined administration includes co-administration, using separate formulations or a single therapeutic formulation, and consecutive administration in either order, wherein preferably there is a time period while both (or all) active agents simultaneously exert their biological activities.

A method of production of the patient specific therapeutic compositions of the present invention includes formulating the patient specific therapeutic composition as a patient specific dose, and providing the patient specific dose in a container having a sterile access port. When the effector molecular conjugated with the monoclonal antibody is a radioisotope, the container may be radiation shielded or may be stored within a radiation shielded outer vessel. The patient specific therapeutic composition may then be frozen to a temperature $\leq -20°$ C. for storage and/or shipping.

The compositions of the present invention may be provided as an article of manufacture containing materials useful for the treatment of the diseases or disorders described above. Thus, the present invention also provides an article of manufacture comprising a container having a sterile access port and containing a patient specific therapeutic composition provided as a patient specific dose. The patient specific therapeutic composition comprises a monoclonal antibody having a labeled fraction and an unlabeled fraction, and a pharmaceutically acceptable carrier. The patient specific therapeutic composition may be any of the compositions described or disclosed herein.

The article of manufacture may comprise a container and a label or package insert on or associated with the container. Suitable containers include, for example, bottles, vials, syringes, etc. The containers may be formed from a variety of materials such as glass or plastic. The container holds or contains the patient specific therapeutic composition which is effective for treating the disease or disorder of choice and may have a sterile access port. For example, the container may be an intravenous solution bag or a vial having a stopper pierceable by a hypodermic injection needle or cannula. When the effector molecular conjugated with the monoclonal antibody is a radioisotope, the container may be radiation shielded or may be stored within a radiation shielded outer vessel.

The composition provided with the article of manufacture may comprise more than one active agent or more than one composition. The label or package insert may indicate that the composition is used for treating a patient having or predisposed to a disease treatable by administration of the composition. For example, the package insert may indicate that lymophoma or leukemia may be treated by the composition which comprises a monoclonal antibody which is at least partially labeled with an effector molecule such as those listed hereinabove, or other conditions or treatment wherein inhibition of certain cell types is desirable, such as autoimmune disease, transplant, gene therapy, cell therapy or inflammatory condition. The article of manufacture may further comprise other materials desirable from a commercial and user standpoint, including other filters, needles, fluid lines, and carriers.

EXAMPLES

Example 1—Administration of $^{131}$I-BC8

Dosimetric and therapeutic doses of a patient specific therapeutic composition comprising $^{131}$I-BC8 and BC8 were formulated as 45 mL ready to administer, parenteral formulations in a 50 mL glass vial, and were stored at −20° C. All dilutions to formulate the dosimetric and therapeutic doses were performed during manufacture of the patient specific therapeutic composition from stocks of BC8 and $^{131}$I-BC8 labelled at high specific activity. Dosimetry dose vials were stored for up to seven (7) days at −20° C. from the time of manufacture, while therapeutic dose vials were stored for up to three (3) days at −20° C. from the time of manufacture, during which time these may be shipped frozen to the clinical sites, such as on wet or dry ice. Prior to intravenous infusion, vials of the patient specific therapeutic composition comprising the $^{131}$I-BC8 were thawed to room temperature, and were administered to the patient at rates of up to 7.5 mg per hour. In certain instances, the patient may be pre-medicated prior to administration of the patient specific therapeutic composition to minimize adverse immunologic responses.

The intravenous delivery system for this example utilized the commercially available Alaris™ Model 8100 pump from CAREFUSION. The infusion set and supplementary supplies utilized for dose administration are described in Table 1. The system of this example dilutes the patient specific therapeutic composition in-line with sterile, 0.9% Sodium Chloride Injection, USP (normal saline).

TABLE 1

Infusion Set Kit Parameters

| Item # | Name | Qnty | Vendor | Ref. # | Description | DEHP | Latex | Priming volume (mL) |
|---|---|---|---|---|---|---|---|---|
| 1 | Microbore extension set | 1 | B.Braun | V5450 | 31 inches, Microbore extension set, (male/male), 50/case | N/A | free | 0.6 |
| 2 | Infusion set, saline line | 1 | CareFusion | 2204-0007 | 47 inches, no piggypack option, 20/case | non | free | 14 |
| 3 | Smartsite infusion set | 1 | CareFusion | 24001-0007 | 47 inches, needle free valve, 20/case | non | free | 14 |
| 4 | Microbore extension set | 1 | CareFusion | MZ9265 | 6 inches, 2 IV connectors, 50/case | non | free | 0.4 |
| 5 | Extension set | 1 | CareFusion | 30914 | 60 inches, Microbore tubing, 100/case | non | free | 0.55 |
| 6 | Aspirating needle | 1 | International medical industries | 32-21 | 19-gauge · 8.89-cm (3.5-in), 100/Box | N/A | N/A | N/A |
| 7 | Needle | 1 | Atlantic medical supply | REF305175 | BD PrecisionGlide ™, 20 G 100/Box | N/A | N/A | N/A |
| 8 | Cartridge | 1 | Waters | JJAN20229 | Sep-Pak Plus, 50/Box | N/A | N/A | N/A |
| 9 | Syringe filter | 1 | Millipore | SLGL0250S | 0.22 uM, Millex ® (MCE), 50/Box | N/A | N/A | N/A |
| 10 | A-clamp | 3 | Davon medical | A-110 | Dravon A-clamp Tube Occluding Forcep, 100/Box | N/A | N/A | N/A |

Preparation for the Dosimetric Dose

A dosimetric dose of the patient specific therapeutic composition was administered to patients in an ambulatory setting. The dosimetry dose was delivered to the medical center in a single glass vial enclosed in a lead pig (lead storage container). The patient specific therapeutic composition was prepared for patient infusion by transferring the vial from the original lead pig to another lead pig stored at room temperature using tongs remotely. The vial was allowed to equilibrate to room temperature (15° to 30° C.) for 2.5 hours. This was sufficient time for complete thawing of the contents. The dose was assayed (for radioactivity) to confirm the activity of the radioisotope. The patient specific therapeutic composition in the lead pig was then transported to the patient room via a lead cart. The lead pig lid was replaced with a lead pig lid having an opening on the top.

Dosimetric Infusion

Materials: IV Infusion Set Kit—(Table 1) and patient specific therapeutic composition in the dosimetry dose contained: 45 mL dose volume in a 50 mL vial, up to 30 milliCurie of a radioactivity dose ($^{131}$I labeled BC8 antibody), and 35 mg total BC8 antibody.

Infusion Procedure of the Dosimetric Dose:

The IV infusion set kit was assembled on the dual pump head as shown in the FIG. 1. The vial containing the dosimetric dose of the patient specific therapeutic composition was vented with a venting unit by connecting a 20-gauge 2.54 cm (1 inch) needle (Part 7, Atlantic Medical Supply, REF305175), a Sep-Pak Plus cartridge (Part 8, Waters, JJAN20229) and a 0.22 µM syringe filter (Part 9, Millipore, SLGL0250S) to prevent the release of volatile iodine.

After the venting unit was inserted to the dose vial, a sterile aspirating 19G needle (Part 6, International Medical Industries, model 32-21) was attached to a male/male Microbore extension set (Part 1, B. Braun, V5450). The opposite end of the aspirating needle was attached to the Y connector closest to the primary infusion line (Part 3, CareFusion, 24001-0007) of Channel A (Alaris™ Model 8100) leading from the saline bag (any size same or larger than 100 mL) to the infusion pump. Gravity was allowed to prime the microbore extension set and the aspirating needle followed by clamping the primary infusion set above Channel A with a roller clamp or A-clamp (Part 10, Davon Medical, A-110). Afterward, the microbore extension set was clamped with an A-clamp (Part 10, Davon Medical, A-110).

The aspiring needle (Part 6, International Medical Industries, model 32-21) was inserted to the bottom of vial containing the dosimetry dose of the patient specific radiotherapeutic composition. The primary infusion set (Part 3, CareFusion, 24001-0007) was loaded to channel A (pump 30 in FIG. 1). For channel B (pump 32 in FIG. 1), a 1000 mL normal saline bag was connected with the second primary infusion set (Part 2, CareFusion, 2204-0007). The primary infusion set was primed with saline and then loaded into Channel B (Alaris™ Model 8100). The pump was then ready for infusion of the patient specific radiotherapeutic composition.

The infusion pump settings and administration process of the dosimetric dose of the patient specific therapeutic composition were as follows:

1. Press system ON button on right side of Point of Care Unit (Alaris™, Module 8015)
2. New Patient—yes, input patient's name; no, select from records.
3. To begin programming, first press the "CHANNEL SELECT" button to select Channel A.
4. For Infusion:
   a. Make sure tubing is clamped off above Channel A. Choose patient specific therapeutic composition dosimetric dose.
   b. Enter the infusion rate and VTBI (volume to be infused) for Channel A—Infusion rate: 9 mL/h; VTBI: 43 mL to 45 mL.
   c. Simultaneously enter the infusion rate and VTBI for normal saline from Channel B (81 mL/h, 387 mL).
   d. When infusion is complete, clamp off Microbore extension set, and open the primary infusion line (Part 3, CareFusion, 24001-0007) on Channel A.
   e. Enter new infusion rate and VTBI (volume to be infused) for Channel A: Infusion rate: 9 mL/h; VTBI: 9 mL
   f. Simultaneously enter the infusion rate and VTBI for normal saline from Channel B (81 mL/h, 81 mL).
   g. Start infusion with a total infusion duration is 342 min (5.78 h)

After infusion, flush and disconnect all the tubing and place in a Ziploc bag and record the radioactivity assayed from the dose calibrator (decay corrected to the initial starting time). Measure and record the radioactivity of the patient specific therapeutic composition vial as assayed with the dose calibrator (setup for $^{131}$I decay corrected to the initial starting time). Calculate and record the dose delivered to the patient by subtracting the residual activity in vial and the infusion set components from the activity of patient specific therapeutic composition in the vial prior to infusion. Discard all materials used to deliver patient specific therapeutic composition in accordance with local, state, and federal regulations governing radioactive and biohazardous waste.

Preparation for the Therapeutic Dose

The therapeutic dose was administered to patients in an inpatient setting using all necessary radiation protection including a radiation isolation room. The patient specific therapeutic composition was delivered in a single 50 mL vial enclosed in a lead pig. To prepare the patient specific therapeutic composition for injection, the lead pig containing the enclosed vial was removed from the −20° C. shipper and placed at room temperature (15° C.-30° C.) for 2.5 hours in a room temperature lead pig. This was sufficient time for complete thawing of the contents before initiating administration to the patient. The dose was assayed to confirm the activity. The patient specific therapeutic composition in the lead pig was transported to the patient room via a lead cart. The lead pig lid was replaced with a lead pig lid with an opening on the top.

Therapeutic Infusion

Materials: IV infusion set Kit—(Table 1, same as dosimetric infusion kit). The therapeutic dose of the patient specific therapeutic composition was customized for each patient. That is, for each therapeutic dose, the radioactivity dose was determined based on biodistribution of the dosimetric dose of the patient specific radiotherapeutic composition, and the antibody dose was calculated by a patient body weight. The therapeutic doses are custom manufactured and contain the following: 45 mL dose volume in a 50 mL vial, 100-1,500 mCi of radioactivity dose ($^{131}$I), and "XX" mg of the BC8 antibody. The protein content (mg) was generally calculated as 0.5 mg/kg patient body weight.

Infusion Procedure of the Therapeutic Dose:

Assemble the IV Kit on the dual pump head as shown in the FIG. 1 (same as dosimetric infusion setup). The vial containing the therapeutic dose of the patient specific therapeutic composition was vented with a venting unit by connecting a 20-gauge 2.54 cm (1 inch) needle (Part 7, Atlantic Medical Supply, REF305175), a Sep-Pak Plus cartridge (Part 8, Waters, JJAN20229) and a 0.22 µM syringe filter (Part 9, Millipore, SLGL0250S) to prevent the release of volatile iodine.

After the venting unit was inserted to the dose vial, a sterile aspirating 19G needle (Part 6, International Medical Industries, model 32-21) was attached to a male/male Microbore extension set (Part 1, B. Braun, V5450). The opposite end of the aspirating needle was attached to the Y connector closest to the primary infusion line (Part 3, CareFusion, 24001-0007) of Channel A (Alaris™ Model 8100) leading from the saline bag (any size same or larger than 100 mL) to the infusion pump. Gravity was allowed to prime the microbore extension set and the aspirating needle followed by clamping the primary infusion set above channel A with a roller clamp or A-clamp (Part 10, Davon Medical, A-110). Afterward, the microbore extension set was clamped with A-clamp (Part 10, Davon Medical, A-110).

An aspiring needle (Part 6, International Medical Industries, model 32-21) was inserted to the bottom of the vial containing the dosimetry dose of the patient specific radiotherapeutic composition. The primary infusion set (Part 3, CareFusion, 24001-0007) was loaded to channel A (pump 30 in FIG. 1). For channel B (pump 32 in FIG. 1), a 1000 mL normal saline bag was connected with the second primary infusion set (Part 2, CareFusion, 2204-0007). The primary infusion set was primed with saline and then loaded into Channel B (Alaris™ Model 8100). The pump was then ready for patient specific therapeutic composition infusion.

The infusion pump settings and administration process of the therapeutic dose of the patient specific therapeutic composition were as follows:
1. Press system ON button on right side of Point of Care Unit (Alaris™, Module 8015)
2. New Patient—yes, input patient's name; no, select from records
3. To begin programming first press the "CHANNEL SELECT" button on to select Channel A.
4. For Infusion:
   a. Make sure tubing is clamped off above Channel A. Choose "therapeutic dose" for the patient specific therapeutic composition.
   b. Enter infusion rate and VTBI (volume to be infused) for Channel A: Infusion rate: 43 mL to 45 mL*7.5 mg/h/xx mg=yy mL/h; VTBI: 43 mL
   c. Simultaneously enter rate and VTBI for normal saline from Channel B (9*yy mL/h, 387 mL).
   d. When infusion is complete, clamp off Microbore extension set, and open the primary infusion line (Part 3, CareFusion, 24001-0007) on Channel A.
   e. Enter new infusion rate and VTBI (volume to be infused) for Channel A: Infusion rate: yy mL/h; VTBI: yy mL.
   f. Simultaneously enter rate and VTBI for normal saline from Channel B (9*yy mL/h, 9*yy mL).
   g. Start infusion and the total infusion duration is (43/yy+1) h After infusion, flush and disconnect all the tubing and place in a Ziploc bag and record the radioactivity assayed from the dose calibrator (decay corrected to the initial starting time). Measure and record the radioactivity the vial which contained the patient specific therapeutic composition as assayed with the dose calibrator (setup for $^{131}$I, decay corrected to the initial starting time). Calculate and record the dose delivered to the patient by subtracting the residual activity in vial and the infusion set components from the activity of patient specific therapeutic composition in the vial prior to infusion. Discard all materials used to deliver patient specific therapeutic composition in accordance with local, state, and federal regulations governing radioactive and biohazardous waste.

Example 2—Administration of $^{90}$Y-BC8

Dosimetric and therapeutic doses of a patient specific therapeutic composition comprising $^{90}$Y-BC8 and BC8 are formulated as 45 mL ready to administer, parenteral formulations in a 50 mL glass vial, and are stored at −20° C. All dilutions to formulate the dosimetric and therapeutic doses are performed during manufacture of the patient specific therapeutic composition from stocks of BC8 and $^{90}$Y-BC8 labelled at high specific activity. Protein amounts and radioactivity doses for each formulation are as described in Example 1. Furthermore, storage, thawing, and infusion are as described in Example 1.

Example 3—Administration of $^{77}$Lu-BC8

Dosimetric and therapeutic doses of a patient specific therapeutic composition comprising $^{177}$Lu-BC8 and BC8 are formulated as 45 mL ready to administer, parenteral formulations in a 50 mL glass vial, and are stored at −20° C. All dilutions to formulate the dosimetric and therapeutic doses are performed during manufacture of the patient specific therapeutic composition from stocks of BC8 and $^{177}$Lu-BC8 labelled at high specific activity. Protein amounts and radioactivity doses for each formulation are as described in Example 1. Furthermore, storage, thawing, and infusion are as described in Example 1.

Example 4—Administration of $^{186}$Re-BC8

Dosimetric and therapeutic doses of a patient specific therapeutic composition comprising $^{186}$Re-BC8 and BC8 are formulated as 45 mL ready to administer, parenteral formulations in a 50 mL glass vial, and are stored at −20° C. All dilutions to formulate the dosimetric and therapeutic doses are performed during manufacture of the patient specific therapeutic composition from stocks of BC8 and $^{186}$Re-BC8 labelled at high specific activity. Protein amounts and radioactivity doses for each formulation are as described in Example 1. Furthermore, storage, thawing, and infusion are as described in Example 1.

Example 5—Administration of BC8-Paclitaxel

A Therapeutic dose of a patient specific therapeutic composition comprising paclitaxel conjugated BC8 (Paclitaxel-BC8) and unlabeled BC8 is formulated as a 45 mL ready to administer, parenteral formulations in a 50 mL glass vial, and is stored at −20° C. All dilutions to formulate the therapeutic dose are performed during manufacture of the patient specific therapeutic composition from stocks of BC8 and Ricin-BC8. Total protein amounts for the monoclonal antibody are as described in Example 1. Doses of the effector molecule paclitaxel are in the range of 15 to 275 mg/m$^2$ (total surface area of the patient). Storage, thawing, and infusion are as described in Example 1.

Example 6—Administration of $^{131}$I-HuM195

Dosimetric and therapeutic doses of a patient specific therapeutic composition comprising $^{131}$I-HuM195 and HuM195 were formulated as 45 mL ready to administer, parenteral formulations in a 50 mL glass vial, and were stored at −20° C. All dilutions to formulate the dosimetric and therapeutic doses were performed during manufacture of the patient specific therapeutic composition from stocks of MuH195 and $^{131}$I-HuM195 labelled at high specific activity. Protein amounts and radioactivity doses for each formulation are as described in Example 1. Furthermore, storage, thawing, and infusion are as described in Example 1.

Example 7—Administration of HuM195-Calicheamicin

A Therapeutic dose of a patient specific therapeutic composition comprising calicheamicin conjugated HuM195 (calicheamicin-HuM195) and unlabeled HuM195 is formulated as a 45 mL ready to administer, parenteral formulations in a 50 mL glass vial, and is stored at −20° C. All dilutions to formulate the therapeutic dose are performed during manufacture of the patient specific therapeutic composition from stocks of HuM195 and calicheamicin-HuM195. Total protein amounts for the monoclonal antibody are as described in Example 1. Doses of the effector molecule calicheamicin are in the range of 1 to 10 mg/m$^2$ (total surface area of the patient). Storage, thawing, and infusion are as described in Example 1.

Example 8—Administration of Anti-CD20-Epithilone

A Therapeutic dose of a patient specific therapeutic composition comprising epithilone conjugated anti-CD20 (epithilone-anti-CD20) and unlabeled anti-CD20 is formulated as a 45 mL ready to administer, parenteral formulations in a 50 mL glass vial, and is stored at −20° C. All dilutions to formulate the therapeutic dose are performed during manufacture of the patient specific therapeutic composition from stocks of anti-CD20 and epithilone-anti-CD20. Total protein amounts for the monoclonal antibody are as described in Example 1. Doses of the effector molecule epithilone are in the range of 10 to 20 mg/m$^2$ (total surface area of the patient). Storage, thawing, and infusion are as described in Example 1.

Each of the characteristics and examples described above, and combinations thereof, may be said to be encompassed by the present invention. The present invention is thus drawn to the following non-limiting aspects:

(1) A patient specific therapeutic composition provided in a single dose container, the composition comprising: a monoclonal antibody comprising: a labeled fraction, wherein the label comprises one of a radiolabel or a drug, and an unlabeled fraction; and a pharmaceutically acceptable carrier, wherein a dose of the label in the labeled fraction of the monoclonal antibody and a total protein amount of the monoclonal antibody depend on at least one patient specific parameter, wherein the at least one patient specific parameter includes a patient weight, a patient age, a patient height, a patient gender, a patient medical condition, and a patient medical history, and wherein a total volume of the patient specific therapeutic agent is wholly deliverable to a patient in one treatment session.

(2) The composition according to aspect 1, wherein the label comprises a beta or gamma emitting radiolabel.

(3) The composition according to aspect 2, wherein the beta emitting radiolabel comprises Iodine 131, Yttrium 90, Lutentium 177, Rhenium 186, or Rhenium 188, and the gamma emitting radiolabel comprises 125 Iodine or 123 Iodine.

(4) The composition according to aspect 1, wherein the label comprises a drug selected from a chemotherapeutic agent or cytotoxin.

(5) The composition according to any of aspects 1 to 4, wherein the total volume is a volume of between 5 mL and 100 mL.

(6) The composition according to any of aspects 1 to 8, that is administered intravenously, intramuscularly, or subcutaneously to the patient.

(7) The composition according to any of aspects 1 to 6, wherein the monoclonal antibody binds specifically to a CD45 antigen, a CD33 antigen, a CD22 antigen, a CD20 antigen, or a combination thereof.

(8) The composition according to any of aspects 1 to 6, wherein the monoclonal antibody is BC8, which binds to the CD45 antigen.

(9) The composition according to any of aspects 1 to 8, for use as a medicament for the ablation of bone marrow cells in cancer patients to prepare them for donor bone marrow transplant.

(10) The composition according to any of aspects 1 to 6, wherein the monoclonal antibody comprises an $^{131}$I-BC8, wherein the radiation dose is either of: a dosimetry dose of up to 30 milliCuries, the total protein amount is between 25 mg and 45 mg, and the volume is about 45 mL, or a therapeutic dose of between 100 milliCuries and 1500 milliCuries and the total protein amount is between 0.4 mg/kg patient weight to 0.6 mg/kg patient weight.

(11) The composition according to and of aspects 1 to 6, wherein the monoclonal antibody is HuM195, which binds specifically to a CD33 antigen.

(12) The composition according to aspect 11, for use as a medicament for the treatment of Acute Myeloid Leukemia.

(13) the composition according to any of aspects 1 to 6, wherein the monoclonal antibody comprises an $^{131}$I-HuM195, wherein the radiation dose is either of: a dosimetry dose of up to 30 milliCuries, the total protein amount is between 25 mg and 45 mg, and the volume is about 45 mL, or a therapeutic dose of between 100 milliCuries and 1500 milliCuries and the total protein amount is between 0.4 mg/kg patient weight to 0.6 mg/kg patient weight.

(14) A method of administration of the patient specific therapeutic composition according to any of aspects 1 to 13, the method comprising:

administering the total volume of the patient specific therapeutic composition to a patient through a fluid path, wherein the fluid path includes a therapeutic agent specific portion; and flushing the fluid path, with the exception of the therapeutic agent specific portion, with normal saline after administration of the patient specific therapeutic composition, wherein the patient specific therapeutic composition is administered intravenously, intramuscularly, or subcutaneously to the patient for treatment of a leukemia, wherein the composition includes a patient specific dose, and wherein, after administering the total volume of the patient specific therapeutic composition, no measurable volume of the patient specific therapeutic composition remains in the fluid path.

(15) The method of administration according to aspect 14, wherein the patient specific therapeutic composition comprises a radioactive label and is supplied in a lead shielded container which is stored at −20° C., wherein before the step of administering the patient specific therapeutic composition, the method further comprises:

thawing the container for at least 1 hour at room temperature (15° C.-30° C.).

(16) The method of administration according to aspects 14 or 15, wherein after the step of thawing the vial containing the patient specific therapeutic composition, the method further comprises:

inserting a vent in the container, wherein the vent includes a cannula to pierce a septum on the container and a filter to prevent release of any volatile radiolabel from the container.

(17) The method of administration according to any of aspects 14 to 16, wherein the administration of the total volume of the patient specific therapeutic composition is at a rate of up to 7.5 mg of protein per hour.

(18) A method of production of the patient specific therapeutic composition according to any of aspects 1 to 13, the method comprising:

formulating the patient specific therapeutic composition as a patient specific dose in a total volume of between 5 mL and 100 mL; and providing the patient specific dose in a container having a sterile access port.

(19) The method of production according to aspect 18, wherein the patient specific therapeutic composition is frozen to a temperature ≤−20° C.

An article of manufacture comprising: a container having a sterile access port and comprising a patient specific therapeutic composition according to any of aspects 1 to 13; and a label or package insert on or associated with the container.

What is claimed is:

1. A patient specific therapeutic composition provided in a single dose container for administration to a specific patient, the composition comprising:
   a monoclonal antibody comprising:
      a labeled fraction, wherein the label comprises a radiation emitting radionuclide, and
      an unlabeled fraction; and
   a pharmaceutically acceptable carrier,
wherein each of a radiation dose of the radionuclide in the labeled fraction of the monoclonal antibody and a total protein amount of the monoclonal antibody depend on at least one parameter of the specific patient, wherein the at least one parameter includes a patient weight, a patient age, a patient height, a patient gender, a patient medical condition, a patient medical history, or a combination thereof, and wherein a total volume of the patient specific therapeutic composition is to be wholly administered to the specific patient in one treatment session, wherein the total volume is 40 mL to 50 mL.

2. The composition of claim 1, wherein the radionuclide comprises Iodine 131, Iodine 125, Iodine 123, Yttrium 90, Lutetium 177, Rhenium 186, Rhenium 188, or a combination thereof.

3. The composition of claim 1, wherein the monoclonal antibody binds specifically to a CD45 antigen, a CD33 antigen, a CD22 antigen, a CD20 antigen, or a combination thereof.

4. The composition of claim 3, wherein the monoclonal antibody is BC8, which binds to the CD45 antigen.

5. The composition of claim 4, wherein the total protein amount and the radiation dose of the radionuclide are for ablation of bone marrow cells in the specific patient to prepare the specific patient for donor bone marrow transplant.

6. The composition of claim 3, wherein the monoclonal antibody is HuM195, which binds specifically to a CD33 antigen.

7. The composition of claim 6, wherein the total protein amount and the radiation dose of the radionuclide are for the treatment of Acute Myeloid Leukemia.

8. A patient specific therapeutic composition provided in a single dose container for administration to a specific patient, the composition comprising:
   a monoclonal antibody in a pharmaceutically acceptable carrier, wherein the monoclonal antibody comprises a labeled fraction and an unlabeled fraction, wherein the label comprises a radiation emitting radionuclide,
   wherein each of a radiation dose of the radionuclide in the labeled fraction and a total protein amount of the monoclonal antibody depend on at least one parameter of the specific patient, wherein the at least one parameter includes a patient weight, a patient age, a patient height, a patient gender, a patient medical condition, a patient medical history, or a combination thereof,
   wherein a total volume of the composition is to be wholly administered to the specific patient in one treatment session, and
   wherein the composition is to be administered intravenously, intramuscularly, or subcutaneously to the specific patient, wherein the monoclonal antibody comprises $^{131}$I-labeled BC8 and unlabeled BC8, wherein the radiation dose is either of:
      a dosimetry dose of up to 30 milliCuries, the total protein amount is between 25 mg and 45 mg, and the total volume is about 45 mL, or
      a therapeutic dose of between 100 milliCuries and 1500 milliCuries, the total protein amount is 0.4 mg/kg patient weight to 0.6 mg/kg patient weight and the total volume is 40 ml to 50 ml.

9. The composition of claim 8, wherein the total protein amount and the radiation dose of the radionuclide are for ablation of bone marrow cells in the specific patient to prepare the specific patient for donor bone marrow transplant.

10. A patient specific therapeutic composition provided in a single dose container for administration to a specific patient, the composition comprising:
   a monoclonal antibody in a pharmaceutically acceptable carrier, wherein the monoclonal antibody comprises a labeled fraction and an unlabeled fraction, wherein the label comprises a radiation emitting radionuclide,
   wherein each of a radiation dose of the radionuclide in the labeled fraction and a total protein amount of the monoclonal antibody depend on at least one parameter of the specific patient, wherein the at least one parameter includes a patient weight, a patient age, a patient height, a patient gender, a patient medical condition, a patient medical history, or a combination thereof,
   wherein a total volume of the composition is to be wholly administered to the specific patient in one treatment session, and
   wherein the composition is to be administered intravenously, intramuscularly, or subcutaneously to the specific patient, wherein the monoclonal antibody comprises $^{131}$I-labeled HuM195 and unlabeled HuM195, wherein the radiation dose is either of:
      a dosimetry dose of up to 30 milliCuries, the total protein amount is between 25 mg and 45 mg, and the total volume is about 45 mL, or
      a therapeutic dose of between 100 milliCuries and 1500 milliCuries and the total protein amount is 0.4 mg/kg patient weight to 0.6 mg/kg patient weight and the total volume is 40 ml to 50 ml.

11. The composition of claim 10, wherein the total protein amount and the radiation dose of the radionuclide are for the treatment of Acute Myeloid Leukemia.

12. An article of manufacture comprising:
   a container having a sterile access port and comprising a patient specific therapeutic composition provided as a patient specific dose, wherein the patient specific therapeutic composition comprises:

a monoclonal antibody comprising a labeled fraction, wherein the label comprises a radiation emitting radionuclide, and an unlabeled fraction; and a pharmaceutically acceptable carrier, wherein each of a radiation dose of the radionuclide in the labeled fraction of the monoclonal antibody and a total protein amount of the monoclonal antibody depend on at least one parameter of a specific patient, wherein the at least one parameter includes a patient weight, a patient age, a patient height, a patient gender, a patient medical condition, a patient medical history, or a combination thereof, and wherein a total volume of the patient specific therapeutic composition is to be wholly administered to the specific patient in one treatment session; and a label or package insert on or associated with the container, wherein the total volume of the patient specific dose is 40 mL to 50 mL.

13. A patient specific therapeutic composition for administration to a specific patient, the composition comprising:

a BC-8 antibody which binds specifically to a CD45 antigen, the antibody comprising:

an $^{131}$I labeled fraction, and an unlabeled fraction; and a pharmaceutically acceptable carrier, wherein each of a radiation dose of the $^{131}$I labeled fraction of the BC-8 antibody and a total protein amount of the BC-8 antibody depend on at least one parameter of the specific patient, wherein the at least one parameter includes a patient weight, a patient age, a patient height, a patient gender, a patient medical condition, or a patient medical history, and wherein a total volume of the patient specific therapeutic composition is 40 mL to 50 mL and is to be wholly administered to the specific patient in one treatment session.

14. A method of administration of the patient specific therapeutic composition of claim 8 to a specific patient, the method comprising:

administering the total volume of the patient specific therapeutic composition to the specific patient through a fluid path, wherein the fluid path includes a therapeutic agent specific portion; and flushing the fluid path, with the exception of the therapeutic agent specific portion, with normal saline after administration of the patient specific therapeutic composition, wherein the patient specific therapeutic composition is administered intravenously, intramuscularly, or subcutaneously to the specific patient for treatment of a leukemia, wherein the composition includes a patient specific dose based on the at least one parameter, and wherein, after administering the total volume of the patient specific therapeutic composition, no measurable volume of the patient specific therapeutic composition remains in the fluid path.

15. The method of administration of claim 14, wherein the single dose container is lead shielded and stored at −20° C., wherein before the step of administering the patient specific therapeutic composition, the method further comprises:

thawing the container for at least 1 hour at a temperature of 15° C.-30° C.

16. The method of administration of claim 15, wherein after the step of thawing the container, the method further comprises:

inserting a vent in the container, wherein the vent includes a cannula to pierce a septum on the container and a filter to prevent release of any volatile radionuclide from the container.

17. The method of administration of claim 14, wherein the administration of the total volume of the patient specific therapeutic composition is at a rate of up to 7.5 mg of protein per hour.

18. A method of production of the patient specific therapeutic composition of claim 8, the method comprising:

formulating the patient specific therapeutic composition as a patient specific dose in a total volume of 40 mL to 50 mL; and providing the patient specific dose in a container having a sterile access port, wherein the patient specific dose depends on the at least one parameter of a specific patient, wherein the at least one parameter includes a patient weight, a patient age, a patient height, a patient gender, a patient medical condition, a patient medical history, or a combination thereof.

19. The method of production of claim 18, wherein the patient specific therapeutic composition is frozen to a temperature ≤−20° C.

* * * * *